United States Patent
Cox (10) Patent No.: US 6,241,758 B1
(45) Date of Patent: Jun. 5, 2001

(54) SELF-EXPANDING STENT DELIVERY SYSTEM AND METHOD OF USE

(75) Inventor: Daniel L. Cox, Palo Alto, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/322,697

(22) Filed: May 28, 1999

(51) Int. Cl.[7] ............................ A61F 2/00; A61M 29/00
(52) U.S. Cl. .......................... 623/1.11; 606/108; 606/198
(58) Field of Search .................................. 606/108, 198; 623/1.11

(56) References Cited

U.S. PATENT DOCUMENTS

| | | |
|---|---|---|
| 4,665,918 | 5/1987 | Garza et al. . |
| 4,681,110 | 7/1987 | Wiktor . |
| 5,201,757 | 4/1993 | Heyn et al. . |
| 5,290,247 * | 3/1994 | Crittenden ............................ 604/171 |
| 5,290,295 * | 3/1994 | Querals et al. ...................... 606/108 |
| 5,609,628 * | 3/1997 | Keranen ................................ 623/1 |
| 5,639,274 * | 6/1997 | Fischell et al. ........................ 604/96 |
| 5,683,451 * | 11/1997 | Lenker et al. .......................... 623/1 |
| 5,735,859 | 4/1998 | Fischell et al. . |
| 5,911,752 * | 6/1999 | Dustrude et al. ....................... 623/1 |
| 5,968,069 * | 10/1999 | Dusbabek et al. .................... 606/194 |
| 6,015,420 * | 1/2000 | Wulfman et al. ..................... 606/168 |
| 6,024,763 * | 2/2000 | Lenker et al. ........................... 623/1 |
| 6,051,021 | 4/2000 | Frid . |
| 6,059,810 | 5/2000 | Brown et al. . |
| 6,086,610 | 7/2000 | Duerig et al. . |

\* cited by examiner

*Primary Examiner*—Gene Mancene
*Assistant Examiner*—Michael B. Priddy
(74) *Attorney, Agent, or Firm*—Fulwider Patton Lee & Utecht, LLP (57) ABSTRACT

A stent delivery system having a stent pusher for delivering and implanting stents is disclosed. The stent delivery system has a tubular catheter with a tapered distal end, and the stent pusher is disposed coaxially therein so that the leading edge is adjacent to the tapered region. A recessed diameter region at the distal end of the stent pusher allows a self-expanding stent to be mounted to the stent pusher and covered by the catheter. As the stent pusher passes through the tapered region, the leading edge bears the resisting load instead of the distal end of the stent during deployment. In another embodiment, an inner sleeve is passed coaxially through an inner lumen of the stent pusher and extends from the distal end of the stent pusher. It is attached to the distal end of the catheter linking movement of the catheter and the inner sleeve. The stent is deployed by pushing on the inner sleeve while holding the stent pusher immobile, which retracts the catheter to expand the stent proximal to distal instead of distal to proximal.

26 Claims, 3 Drawing Sheets

SELF-EXPANDING STENT DELIVERY SYSTEM AND METHOD OF USE

BACKGROUND OF THE INVENTION

This invention is related to the delivery of expandable devices commonly called "stents" within a body lumen such as an artery and the expansion of the stent therein to maintain the patency of the body lumen. The invention is particularly suitable for the delivery of the stents after angioplasty procedures.

Percutaneous transluminal coronary angioplasty (PTCA) is now a widely practiced procedure for treating coronary artery disease. In a typical PTCA procedure, a dilatation catheter having an inflatable, relatively inelastic balloon on the distal end thereof is advanced through a patient's arterial system until the deflated balloon crosses an atherosclerotic lesion to be dilated. The balloon is inflated to a predetermined size with radiopaque liquid at relatively high pressures (e.g., up to 8 atmospheres or more) to compress the atherosclerotic plaque and to dilate the artery in the stenotic region. After dilation the balloon is then deflated so that the catheter can be removed. Due to the enlarged arterial passageway, increased blood flow results.

In typical PCTA procedures, a guiding catheter having a preformed distal end is first percutaneously introduced into the patient's arterial system and advanced until the distal tip of the catheter is disposed in the ostium of a coronary artery. A guide wire is slidably disposed within an inner lumen of a dilatation catheter and both are advanced through the guiding catheter to the distal end thereof. The guide wire is first advanced out of the distal tip of the dilatation catheter into the patient's coronary anatomy until the distal end of the guide wire crosses the lesion to be dilated. The physician usually shapes the distal end of the guide wire to facilitate steering through the patient's tortuous coronary arteries. Once the guide wire is in place, the dilatation catheter is advanced out of the distal tip of the guiding catheter over the guide wire until the deflated balloon on the distal end of the dilatation catheter is positioned across the lesion. The balloon is inflated to a suitable pressure to dilate the stenosis, deflated, and then removed from the patient's vasculature.

For a more detailed description of the angioplasty procedures and the devices used in such procedures, reference is made to U.S. Pat. No. 4,332,254 (Lundquist); U.S. Pat. No. 4,323,071 (Simpson-Robert); U.S. Pat. No. 4,439,185 (Lundquist); U.S. Pat. No. 4,468,224 (Enzmann et al.); U.S. Pat. No. 4,516,972 (Samson); U.S. Pat. No. 4,538,622 (Samson et al.); U.S. Pat. No. 4,554,929 (Samson et al.); U.S. Pat. No. 4,569,347 (Frisbie); U.S. Pat. No. 4,571,240 (Samson et al.); U.S. Pat. No. 4,616,652 (Simpson); U.S. Pat. No. 4,748,982 (Horzewski et al.); U.S. Pat. No. 5,300,085 (Yock); U.S. Pat. No. 5,496,346 (Horzewski et al.); and U.S. Pat. No. 5,626,600 (Horzewski et al.), which are hereby incorporated in their entirety by reference thereto.

On occasion, the inflation of the balloon during angioplasty causes a dissection in the arterial lining, e.g., the stenotic plaque or the arterial intima. When the balloon is deflated after such a dilation, blood can flow between the arterial wall and the dissected lining constricting the flow passage therein or causing a section of the dissected lining, commonly called a "flap," to be forced into the flow passageway thereby partially or completely blocking the blood flow through the artery.

Several methods have been proposed to resecure a dissected lining to the artery wall. For example, the dilatation catheter can be removed after the angioplasty procedure has been performed and replaced with a catheter having an expandable member at the distal end which allows for the perfusion of blood through the expandable member when expanded. In this method, the expanded member presses the dissected tissue lining against the arterial wall for an extended period until the dissected lining is re-secured to the arterial wall. Blood perfuses through the expanded member so that ischemic conditions are minimized or eliminated distal to the expanded member. However, these lining repair procedures usually require leaving the catheter with the expanded member in place for an extended period, e.g., fifteen minutes or more, in order to ensure that the lining has been properly re-secured to the arterial lining. Suitable catheters for this purpose are disclosed in U.S. Pat. No. 4,790,315; U.S. Pat. No. 4,998,539 (Delsanti); U.S. Pat. No. 5,034,001 (Garrison et al.); and U.S. Pat. No. 5,002,560 (Machold et al.), each of which is incorporated herein in their entirety by reference thereto.

Much development work has also been recently performed on the use of expandable stents in situations where long term expansion in an arterial or other bodily lumen is desired, such as in the instances described above. Expandable stents and their method of use are described in, for example, U.S. Pat. No. 5,603,721 (Lau et al.); U.S. Pat. No. 5,421,955 (Lau et al.); U.S. Pat. No. 5,514,154 (Lau et al.); U.S. Pat. No. 4,655,771 (Wallsten); U.S. Pat. No. 4,733,665 (Palmaz); U.S. Pat. No. 4,739,762 (Palmaz); U.S. Pat. No. 4,762,128 (Rosenbluth), Japanese application 57-89859 published Jun. 4, 1982, and European Application 0183372 published Jun. 9, 1986 which are hereby incorporated by reference.

More recent developments include stent delivery systems disclosed in U.S. Pat. No. 5,158,548 to Lau et al. Such a stent delivery system has an expandable stent in a contracted condition positioned on an expandable member, such as an inflatable balloon, disposed on the distal portion of an elongated catheter body. A guide wire extends through an inner lumen within the elongated catheter body and out its distal end. A tubular protective sheath is secured by its distal end to the portion of the guide wire which extends out ofthe distal end of the catheter body and fits over the stent mounted on the expandable member on the distal end of the catheter body.

Another stent delivery system is disclosed in U.S. Pat. No. 5,458,615 to Klemm et al. Such a delivery system includes an elongated delivery sheath and a catheter disposed within an outer lumen of the sheath having an expandable member on its distal extremity. An expandable stent is mounted on the expandable member of the catheter. The distal portion of the sheath tapers down and is tucked within an elastic cone during transport of the stent to a damaged region of the patient's body lumen. A manipulating device is provided on the proximal end of the delivery system to effect relative axial movement between the sheath and the catheter to expose the stent mounted on the expandable member to allow the expansion of the stent by the expansion of the expandable member.

Still another stent delivery system is disclosed in U.S. Pat. No. 5,634,928 to Fischell et al. This integrated catheter system uses a balloon angioplasty catheter placed through a central passageway of a stent delivery catheter to enable balloon angioplasty and stent delivery to be accomplished with a single device. The Lau et al., Klemm et al., and Fischell et al. patents are incorporated by reference herein in their entirety.

Some stent delivery systems use stent pushers to deploy the stent. An example of a stent pusher is shown in U.S. Pat.

No. 4,580,568 to Gianturco. In this device, a stent is compressed to a reduced diameter which is several times smaller than its expanded diameter. The stent is positioned in a passageway in the vascular system by means of a sheath while the stent is retained in the compressed size. A flat-ended catheter/stent pusher is advanced through the sheath to hold the stent in place in the passageway while the sheath is withdrawn from the passageway allowing the stent to expand in the passageway into its expanded shape to hold the passageway open. This technology is also discussed in an article entitled "Tracheobronchial Tree: Expandable Metallic Stents Used In Experimental And Clinical Applications" by Gianturco et al., *Radiology*, vol. 158, pp. 309–12 (published Dec. 5, 1986). The Gianturco patent and article are incorporated by reference herein.

Despite these improvements, there is still a need for an improved stent delivery system that is capable of negotiating tortuous vessels and crossing a tight stenosis.

SUMMARY OF THE INVENTION

The present invention is directed to a method and apparatus for a stent delivery system for delivering an unexpanded stent to a patient's body lumen, the stent delivery system comprising a tubular catheter having a tapered and pliable distal end, a proximal end, and an inner lumen extending therethrough; a rigid cylindrical-shaped stent pusher having a proximal end, and a leading edge at a distal end defining a first diameter, wherein the stent pusher is disposed at least partially within the catheter lumen; a recessed region of the stent pusher underlying the catheter having a second diameter smaller than the first diameter to receive the stent so that the outside diameter of the stent is at most equal, and in the preferred embodiment equivalent, to the first diameter; an inner lumen extending coaxially through the stent pusher; and a guide wire extending through the inner lumen of the stent pusher.

So in the present invention, the leading edge of the stent pusher bears the load encountered when the stent is deployed through the tapered distal end of the catheter. This is preferable to bearing the load directly against the distal end of the stent as would occur in various prior art systems.

In an alternative embodiment of the present invention, the stent delivery system allows the stent to expand proximal to distal instead of distal to proximal as in the preceding exemplary embodiment. To achieve this deployment method, the present invention system further comprises a rigid inner sleeve extending coaxially over the guide wire and through the lumen of the stent pusher, and wherein the inner sleeve has a length longer than the stent pusher and includes a distal end attached to the distal end of the catheter.

To deploy the stent, the cardiologist positions the distal end of the stent delivery system at the lesion, maintains a hold on the stent pusher while pushing the inner sleeve in the distal direction. As the inner sleeve moves in the distal direction, it slides the catheter attached thereto in the distal direction as well. Movement of the catheter thereby slowly exposes first the proximal end of the unexpanded stent and then the distal end of the unexpanded stent.

In various other alternative embodiments, the distal end of the catheter is tapered and may include a longitudinal slit, perforations, or overlapping surfaces forming a spiral. These features enable the distal end of the stent pusher to pass through the distal end of the catheter with ease by minimizing friction or resistance.

The exemplary embodiment of the present invention delivery system is percutaneously introduced into the patient's arterial system in a conventional Seldinger technique commonly employed in PTCA. The guide wire is steerable so that the entire stent delivery assembly can be steered through the patient's arterial system until the stent is positioned at the desired arterial location.

Once the stent is at the desired location, commonly referred to as the target site, the stent is deployed by translating the catheter to uncover the stent. The self-expanding stent then expands to its final shape and size automatically at the target site. If the stent is not self-expanding, a balloon is inflated to expand the stent beyond its elastic limit within the target site, pressing the stent against the arterial lining. The expandable member or balloon is then deflated to disengage the catheter delivery system from the expanded stent and to facilitate its removal from the body lumen. The delivery system of the present invention allows for the rapid and safe deployment of an expandable stent within a patient's vascular system or other body lumen and the quick removal of the delivery system after the stent is expanded at the desired location within the lumen.

These and other advantages of the present invention will become apparent from the following detailed description and the accompanying exemplary drawings.

BRIEF DESCRIPTION OF THE DRAWINGS

FIGS. 3A, 3B, 3C, and 3D are a side, front, front, and side elevational views of a tapered cone located at the distal end of the catheter as shown in FIG. 2. FIGS. 3A and 3B depict a cone with at least one slit.

DETAILED DESCRIPTION OF THE PREFERRED EMBODIMENTS

Figure 1:
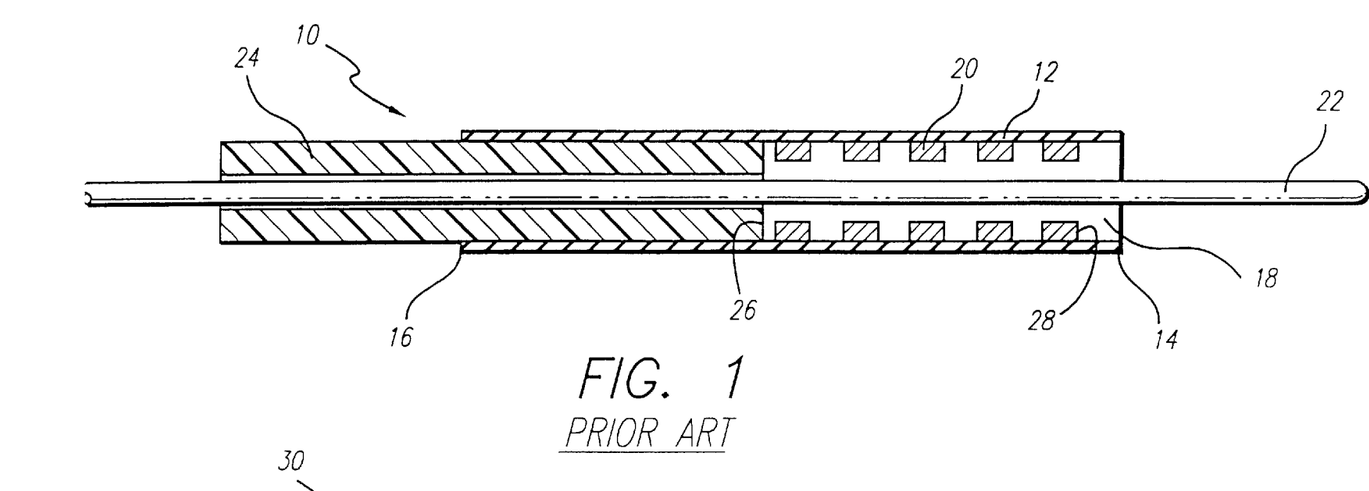
FIG. 1 is a cross-sectional view of a conventional stent delivery system using a stent pusher, an outer catheter, and a stent situated at the distal end of the catheter.

The present invention is directed to a stent delivery system. Current stent delivery systems for self-expanding stents are typically constructed as illustrated in FIG. 1. As seen in the cross-sectional view of FIG. 1, stent delivery system 10 is constructed from tubular shape catheter 12 having distal end 14 and proximal end 16. Within inner lumen 18 of catheter 12 at distal end 14 is self-expanding stent 20. Catheter 12 thus keeps self-expanding stent 20 from expanding until needed.

Stent delivery system 10 is tracked over guide wire 22. Moving along uide wire 22 is stent pusher 24 abutting proximal end 26 of stent 20. Stent pusher 24 s used to push stent 20 in order to hold it in place while catheter 12 is retracted roximally allowing stent 20 to be exposed to the ambient environment and to expand from the distal to the proximal end as stent 20 exits catheter 12 via distal end 14. An example of a stent delivery system similar to that described is disclosed in, for example, U.S. Pat. No. 4,580, 568 to Gianturco.

As depicted in FIG. 1, because the diameter of stent 20 with catheter 12 surrounding it is substantially greater than the diameter of guide wire 22, there is a large, abrupt diameter increase, transitioning from guide wire 22 to catheter 12. This blunt distal end 14 of catheter 12 can be a significant limitation in negotiating tortuosity in a vessel or in crossing a tight stenosis. It is therefore desirable to make this transition smoother and less abrupt.

Figure 2:
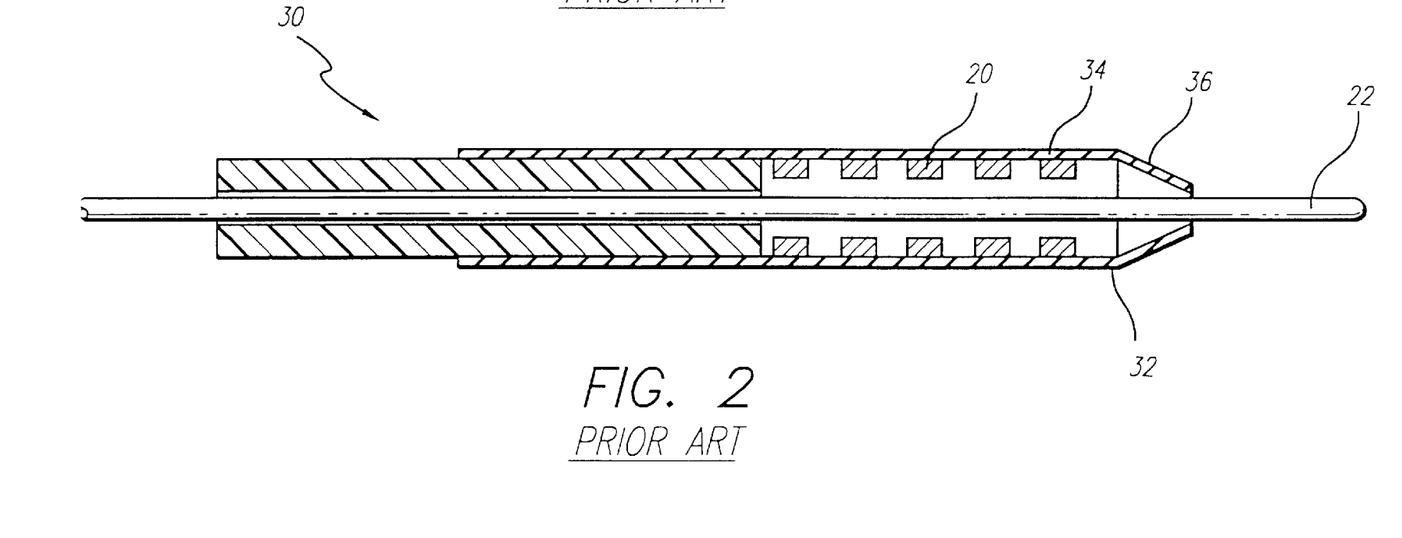
FIG. 2 is a cross-sectional view of another conventional stent delivery system wherein the distal end of the catheter is tapered.

In a conventional design shown in the cross-sectional view of FIG. 2, the transition has been modified with a taper. Specifically, in stent delivery system 30 shown in FIG. 2, distal end 32 of catheter 34 is tapered at region 36. With a tapered distal end 32, catheter 34 provides a smooth and gradually decreasing transition from the outside diameter of catheter 32 to the outside diameter guide wire 22. Tapered region 36 can be made by heating and stretching catheter 32 to a smaller diameter. It is also possible to bond a tapered cone onto distal end 32 of catheter 34. Such a construction is shown in, for example, U.S. Pat. No. 5,458,615 to Klemm et al.

On the other hand, the presence of tapered region 36 presents problems for deployment of stent 20. For instance, distal end 28 of stent 20 bears a great load when it must push open tapered region 36 during deployment. This load might distort the profile of stent 20, cause stent 20 to hang due to friction with tapered region 36, damage a stent strut, etc.

Figure 4:
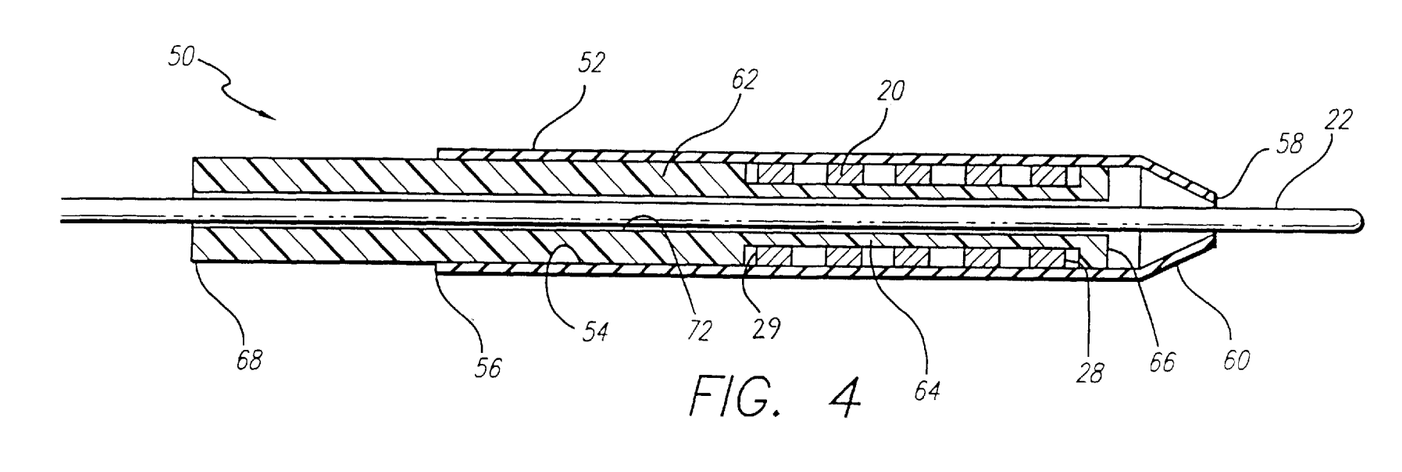
FIG. 4 is a cross-sectional view of a preferred embodiment of the present invention showing a stent pusher loaded with a stent covered by a catheter having a tapered distal end with a guide wire passing therethrough.

In order to minimize the potential for such problems, the present invention stent delivery system 50 employs a unique stent pusher design. FIG. 4 provides a cross-sectional view of a preferred embodiment of the present invention. In this preferred embodiment, stent delivery system 50 comprises tubular catheter 52 having inner lumen 54 extending therethrough leading from proximal end 56 to distal end 58. Distal end 58 further preferably includes tapered region 60.

Catheter 52 partially overlies stent pusher 62 which has a generally cylindrical shape with a recessed region 64 having a reduced diameter. Recessed region 64 is preferably located proximate to distal end 66 of stent pusher 62. Proximal end 68 of stent pusher 62 extends past proximal end 56 of catheter 52 to allow a handhold area for the user or cardiologist.

Unexpanded stent 20 is mounted at recessed region 64 so that the outside diameter of unexpanded stent 20 is at most flush with the outside diameter of stent pusher 62. Stent pusher 62 further includes leading edge 66 adjacent distal end 28 of stent 20. Leading edge 66 may be blunt as shown in FIG. 4, or may have a rounded or a cone shape profile to control engagement with tapered region 60. More importantly, with the presence of leading edge 66, distal end 28 of stent 20 is thereby protected.

Moreover, stent pusher 62 preferably has leading edge 66 that has a diameter as large as the diameter of stent 20. Therefore, the profile of stent 20 is likewise protected.

Leading edge 66 transfers the force encountered to push open tapered region 60 to stent pusher 62 instead of bearing the load directly against distal end 28 of stent 20, as would occur in the prior art configuration shown in FIG. 2. Stent pusher 62 of the present invention thus provides a force bearing structure to protect stent 20.

Stent pusher 62 includes inner lumen 72 extending coaxially along the length thereof. Guide wire 22 passes through inner lumen 72, and stent delivery system 50 tracks over guide wire 22.

Figure 3A:
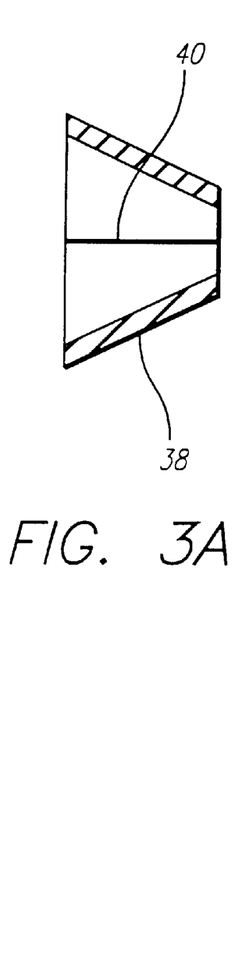
Figure 3B:
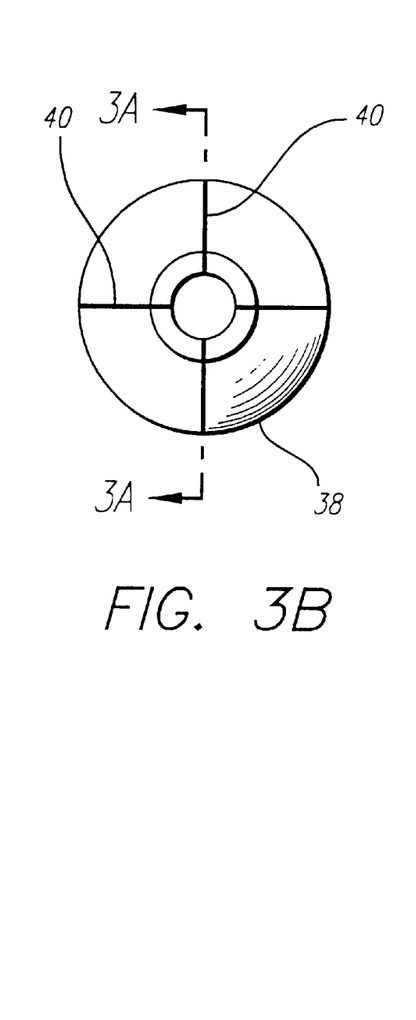

To enhance pushability and maneuverability, tapered region 60 optionally ay be modified as depicted in FIGS. 3A–3D. Tapered region 60 when modified as hown in FIGS. 3A–3D enables free expansion and allows stent 20 to be easily pushed therethrough. In particular, FIGS. 3A and 3B show side and front elevational views of alternative embodiment tapered region 38 that has at least one longitudinal slit 40. As stent 20 moves into tapered region 38 stretching the fabric in that area, slit 40 separates thereby relieving the stress build up. The separating slit also allows easier passage of stent 20 through tapered region 38 with less resistance.

Figure 3C:
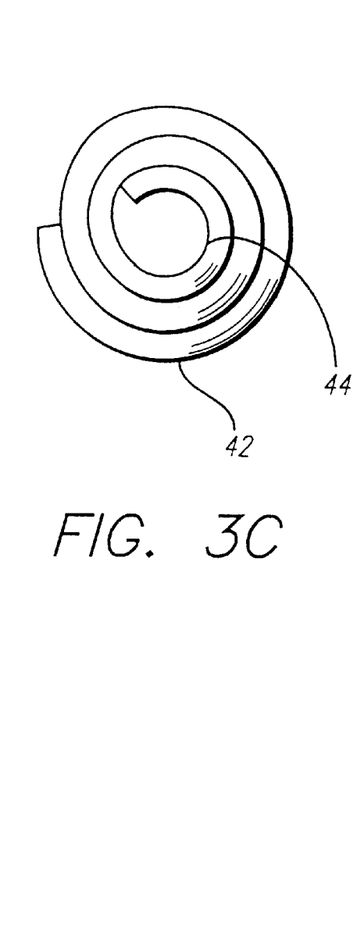
FIG. 3C is a front elevational view of a tapered cone having overlapping surfaces formed into a spiral.

In another alternative embodiment, shown in the front elevational view of FIG. 3C, tapered region 42 includes a rolled up and overlapping area to create spiral 44. Again the goal is to permit material in that area to easily separate to permit passage of stent 20 therethrough. An example of a catheter with such a spiral fold tip is disclosed in U.S. Pat. No. 5,447,503 to Miller.

Figure 3D:
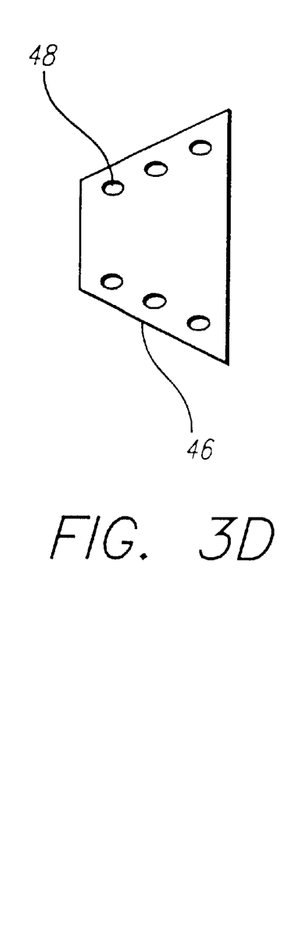
FIG. 3D is a side elevational view of an alternative embodiment cone having perforations and positioned at the distal end of the catheter.

FIG. 3D shows a side elevational view of tapered region 46 of another alternative embodiment catheter having perforations 48. As with the construction shown in FIGS. 3A, 3B, and 3C, perforations 48 allow the diameter of tapered region 46 to increase as stent 20 is pushed therethrough. Perforations 48 thus permit a greater degree of stretching in the material forming tapered region 46 without tearing and with minimal resistance.

Figure 5:
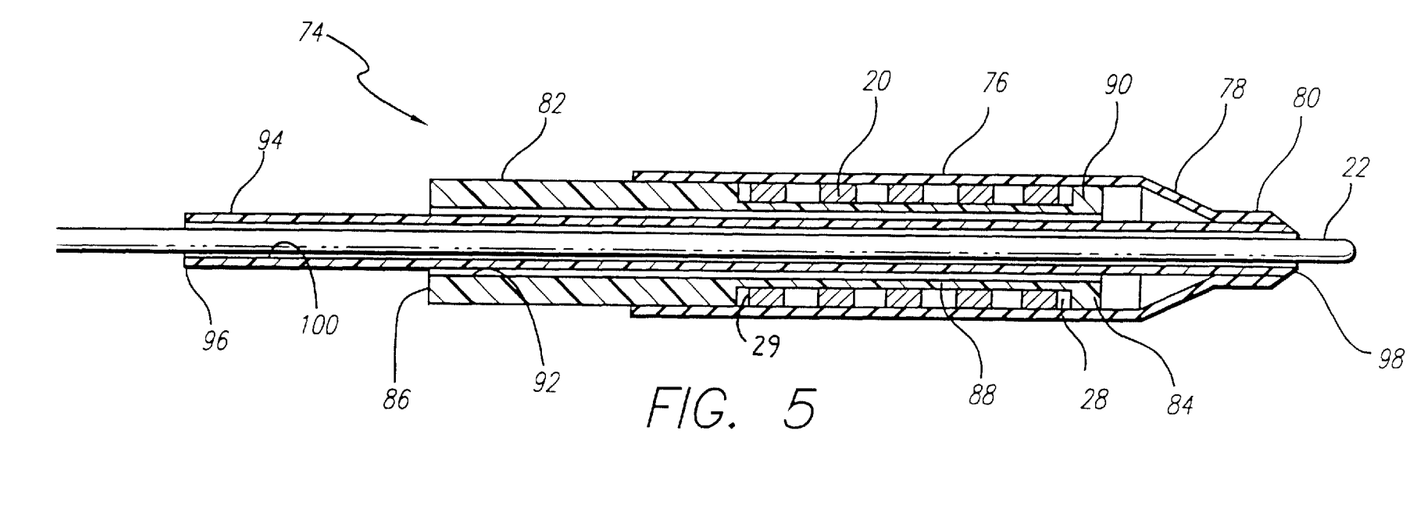
FIG. 5 is a cross-sectional view of an alternative embodiment of the present invention showing a stent pusher and a catheter covering the stent along with an inner sleeve used to retract the catheter to expose the stent from the stent proximal end first.

FIG. 5 provides a cross-sectional view of an alternative embodiment stent delivery system 74. Stent delivery system 74 preferably comprises catheter 76 having tapered region 78 at distal end 80. Partially underlying catheter 76 is stent pusher 82 preferably formed in a cylindrical shape with distal end 84 and proximal end 86. Adjacent distal end 84 is recessed region 88 to which is mounted unexpanded stent 20. Stent pusher 82 further includes leading edge 90 and inner lumen 92 extending along the length thereof.

Passing through inner lumen 92 is inner sleeve 94 having proximal end 96 and distal end 98. Preferably, distal end 80 of catheter 76 engages distal end 98 of inner sleeve 94. The interface may be bonded, mechanically linked, welded, or otherwise attached through processes known in the art. Thus, movement of catheter 76 is directly linked to movement of inner sleeve 94. Inner sleeve 94 preferably is rigid to enhance pushability. Inner sleeve 94 further has inner lumen 100 through which guide wire 22 passes. Stent delivery system 74 tracks over guide wire 22.

Again, in order to minimize the load encountered by distal end 28 of stent 20, the present invention provides leading edge 90, which is connected to or is unitary (one piece) with stent pusher 82, as a load bearing structure. It is noted that edge 90 is load bearing as a puller, but does not protect the edge of the stent as in FIG. 4 because the stent is moving in the opposite direction. Furthermore, the outside diameter of stent 20 as it is mounted to recessed region 88 is preferably equivalent to the outside diameter of leading edge 90 and stent pusher 82. This is preferable because stent 20 is pushing out against catheter 76, and it is sometimes impractical to keep the outside diameter of leading edge 90 always larger than the outside diameter of stent 20. If the two have equivalent diameters within manufacturing tolerances, the object of the invention is still achieved. In an alternative embodiment, the outside diameter of stent 20 as it is mounted to recessed region 88 is at most equal to the outside diameter of leading edge 90 and stent pusher 82.

The alternative embodiment stent delivery system 74 as shown in FIG. 5 operates to allow stent 20 to expand proximal to distal instead of distal to proximal as in the other exemplary embodiments. In operation, catheter 76 is advanced distally off stent 20 by the physician pushing inner sleeve 94 in a distal direction while holding stent pusher 82 immobile. Conceptually speaking, stent pusher 82 is actually a puller in this configuration. In the exemplary embodiment shown in FIG. 5, stent delivery system 74 enjoys a smooth transition at distal tapered region 78 to allow it to negotiate tortuosity freely and to cross lesions smoothly. It can also be very accurately placed on proximal end 29 of stent 20. This is especially useful in ostial lesions or in trying to locate a stent near a bifurcation.

This alternative embodiment does have a larger profile because of the space occupied by inner sleeve 94. This of course assumes that stent 20 itself does not require a larger profile to fit all of its struts. The alternative embodiment of the present invention also requires that the cardiologist check for sufficient space in the vessel distal to the lesion to advance catheter 76 while deploying stent 20. Lastly, this alternative embodiment might not provide as much protection of the distal circulation from emboli that may be loosened from the arterial wall during stent deployment.

In each of the exemplary embodiments, the stent delivery system components may be made from a variety of materials known in the art. Such materials include polyamide, polyetheretherketone (PEEK), polyethylene terephthalate (PET), polytetrafluoroethylene (PTFE), polyolefin, silicone, polyurethane, nylon, or the like. The bond used between the interface of distal end 80 of catheter 76 and distal end 98 of inner sleeve 94 can be any adhesive known in the art, including acrylonitrile-based adhesives. The catheter, inner sleeve, tapered region, and like components should be formed from material of sufficient strength and/or wall thickness so that they retain their cylindrical shape when mounting and removing the delivery system from the stent.

The stent used in the present invention can have any configuration or pattern known in the art and preferably is formed from self-expanding metals including stainless steel or nickel-titanium (both shape memory and stress-induced martensite), or other shape memory or pseudoelastic alloys.

While the present invention has been described herein in terms of certain preferred embodiments, those skilled in the art recognize that various modifications can be made. To be sure, while the present invention has been described herein in terms of delivering an expandable stent to a target site within a patient's body lumen, the delivery system can also be employed to deliver stents to locations within other body lumens such as urethra or Fallopian tubes so that the stents can be expanded to maintain the patency of these body lumens. Various changes and improvements may also be made to the present invention without departing from the scope thereof.

The preceding description and exemplary drawings apply to self-expanding stents and their delivery system. However, the inner sleeve and proximal to distal movement of the sheath of the present invention could be used on balloon expandable stents, and such an application is contemplated. In that case, the stent pusher is omitted.

What is claimed is:

1. A stent delivery system for delivering a stent to a patient's body lumen, comprising:
    a catheter having a tapered and pliable distal end, a proximal end, and an inner lumen;
    a stent pusher having a leading edge at a distal end, a recessed region proximate to the distal end, and a proximal end, wherein the stent pusher is disposed at least partially within the catheter inner lumen, and wherein the stent pusher includes an inner lumen; and
    a stent is disposed on the recessed region.

2. The stent delivery system of claim 1, wherein a guide wire extends through the inner lumen of the stent pusher.

3. The stent delivery system of claim 1, wherein the leading edge includes a diameter that is slightly smaller than the catheter inner lumen diameter.

4. The stent delivery system of claim 1, wherein the tapered distal end of the catheter includes a longitudinal slit.

5. The stent delivery system of claim 1, wherein the tapered distal end of the catheter includes overlapping surfaces forming a spiral.

6. The stent delivery system of claim 1, wherein the system includes a material selected from the group consisting of polyamide, polyetheretherketone (PEEK), polyethylene terephthalate (PET), polytetrafluorethylene (PTFE), polyolefin, silicone, nylon, or polyurethane.

7. A stent delivery system for delivering a stent to a patient's body lumen, comprising:
    a catheter having a tapered and pliable distal end, a proximal end, and an inner lumen, wherein the tapered distal end of the catheter includes perforations;
    a stent pusher having a leading edge at a distal end, a recessed region proximate to the distal end, and a proximal end, wherein the stent pusher is disposed at least partially within the catheter inner lumen, and wherein the stent pusher includes an inner lumen; and
    a stent disposed on the recessed region.

8. A stent delivery system for delivering a stent to a patient's body lumen, comprising:
    a catheter having a tapered and pliable distal end, a proximal end, and an inner lumen;
    a stent pusher having a leading edge at a distal end, a recessed region proximate to the distal end, and a proximal end, wherein the stent pusher is disposed at least partially within the catheter inner lumen, and wherein the stent pusher includes an inner lumen;
    a stent disposed on the recessed region; and
    an inner sleeve disposed coaxially over the guide wire and having a distal end attached to the tapered distal end of the catheter, and wherein the stent pusher is disposed coaxially over the inner sleeve.

9. The stent delivery system of claim 8, wherein the distal end of the inner sleeve is tapered.

10. The stent delivery system of claim 8, wherein the distal end of the inner sleeve extends beyond the tapered distal end of the catheter.

11. A stent delivery system for delivering a stent to a patient's body lumen, comprising:
    a tubular catheter having a tapered and pliable distal end, a proximal end, and an inner lumen extending therethrough;
    a cylindrical-shape stentpusher having a substantially rigid proximal end, and a leading edge at a distal end defining a first diameter, wherein the stent pusher is disposed at least partially within the catheter lumen;
    a recessed region of the stent pusher having a second diameter smaller than the first diameter to receive the stent so that an outside diameter of the stent when disposed about the recessed region is at most equal to the first diameter; and
    an inner lumen extending coaxially through the stent pusher.

12. The stent delivery system of claim 11, wherein a guide wire extends through the inner lumen of the stent pusher.

13. The stent delivery system of claim 11, wherein the outside diameter of the stent is approximately equivalent to the second diameter of the stent pusher.

14. A stent delivery system for delivering a stent to a patient's body lumen, comprising:
   a tubular catheter having a tapered and pliable distal end, a proximal end, and an inner lumen extending therethrough;
   a cylindrical-shape stent pusher having a substantially rigid proximal end, and a leading edge at a distal end defining a first diameter, wherein the stent pusher is disposed at least partially within the catheter lumen;
   a recessed region of the stent pusher having a second diameter smaller than the first diameter to receive the stent sothat an outside diameter of the stent when disposed about the recessed region is at most equal to the first diameter;
   an inner lumen extending coaxially through the stent pusher;
   a guide wire extending through the inner lumen of the stent pusher; and
   an inner sleeve extending coaxially over the guide wire and through the lumen of the stent pusher, and wherein the inner sleeve has a length longer than the stent pusher and includes a distal end attached to the distal end of the catheter.

15. The stent delivery system of claim 14, wherein the inner sleeve is at least partially formed of a rigid material.

16. The stent delivery system of claim 14, wherein the distal end of the inner sleeve includes a taper.

17. The stent delivery system of claim 14, wherein the distal end of the inner sleeve is bonded to the distal end of the catheter.

18. A method for delivering a stent to a patient's body lumen, comprising the steps of:
   providing a tubular catheter having a tapered and pliable distal end, a proximal end, and an inner lumen extending therethrough;
   providing a rigid, cylindrical shape stent pusher having a proximal end, and a leading edge at a distal end defining a first diameter, wherein the stent pusher is disposed at least partially within the catheter inner lumen;
   providing a recessed region of the stent pusher having a second diameter smaller than the first diameter to receive the stent so that an outside diameter of the stent is at most equivalent to the leading edge first diameter;
   providing an inner lumen extending through the stent pusher;
   providing a guide wire extending through the inner lumen of the stent pusher; and
   translating the catheter relative to the stent pusher to expose the stent from within the catheter via the distal end of the catheter.

19. The method of claim 18, wherein the step of translating the catheter further comprises holding the stent pusher stationary and pulling the catheter in a proximal direction.

20. The method of claim 18, wherein the method further comprises providing a longitudinal slit in the tapered distal end of the catheter.

21. The method of claim 18, wherein the method further comprises providing overlapping surfaces forming a spiral in the tapered distal end of the catheter.

22. The method of claim 18, wherein the step of translating the catheter further comprises holding the stent pusher stationary and translating the catheter in a proximal direction.

23. A method for delivering a stent to a patient's body lumen, comprising the steps of:
   providing a tubular catheter having a tapered and pliable distal end, a proximal end, and an inner lumen extending therethrough;
   providing perforations in the tapered distal end of the catheter;
   providing a rigid, cylindrical shape stent pusher having a proximal end, and a leading edge at a distal end defining a first diameter, wherein the stent pusher is disposed at least partially within g the catheter inner lumen;
   providing a recessed region of the stent pusher having a second diameter smaller than the first diameter to receive the stent so that an outside diameter of the stent is at most equivalent to the leading edge first diameter;
   providing an inner lumen extending through the stent pusher;
   providing a guide wire extending through the inner lumen of the sten pusher; and translating the catheter relative to the stent pusher to expose the stent from within the catheter via the distal end of the catheter.

24. A method for delivering a stent to a patient's body lumen, comprising the steps of:
   providing a tubular catheter having a tapered and pliable distal end, a proximal end, and an inner lumen extending therethrough;
   providing a rigid, cylindrical shape stent pusher having a proximal end, and a leading edge at a distal end defining a first diameter, wherein the stent pusher is disposed at least partially within g the catheter inner lumen;
   providing a recessed region of the stent pusher having a second diameter smaller than the first diameter to receive the stent so that an outside diameter of the stent is at most equivalent to the leading edge first diameter;
   providing an inner lumen extending through the stent pusher;
   providing a guide wire extending through the inner lumen of the sten pusher;
   providing a rigid inner sleeve extending coaxially over the wire and through the lumen of the stent pusher, and wherein the inner sleeve has a length longer than the stent pusher and includes a distal end attached to the distal end of the catheter; and
   translating the catheter relative to the stent pusher to expose the stent from within the catheter via the distal end of the catheter.

25. The method of claim 24, wherein the method further comprises translating the inner sleeve in a distal direction, and holding the stent pusher immobile.

26. The method of claim 24, wherein the method further comprises translating the catheter relative to the stent pusher to expose a proximal end of the stent before exposing a distal end of the stent.

* * * * *

UNITED STATES PATENT AND TRADEMARK OFFICE
CERTIFICATE OF CORRECTION

PATENT NO. : 6,241,758 B1   Page 1 of 4
DATED : June 5, 2001
INVENTOR(S) : Daniel L. Cox It is certified that error appears in the above-identified patent and that said Letters Patent is hereby corrected as shown below:

Title page,
Insert Item [56] References Cited;

U.S. PATENT DOCUMENTS

| Number | Date | Inventor |
|---|---|---|
| 4,300,244 | 11/17/81 | Bokros |
| B1 4,323,071 | 05/29/90 | Simpson et al. |
| 4,332,254 | 06/01/82 | Lundquist |
| 4,439,185 | 03/27/84 | Lundquist |
| 4,468,224 | 08/28/84 | Enzmann et al. |
| 4,512,338 | 04/23/85 | Balko et al. |
| 4,516,972 | 05/14/85 | Samson |
| 4,538,622 | 09/03/85 | Samson et al. |
| 4,569,347 | 02/11/86 | Frisbie |
| 4,571,240 | 02/18/86 | Samson et al. |
| 4,580,568 | 04/08/86 | Gianturco |
| 4,616,652 | 10/14/86 | Simpson |
| 4,655,771 | 04/07/87 | Wallsten |
| 4,733,665 | 03/29/88 | Palmaz |
| B1 4,733,665 | 01/11/94 | Palmaz |
| 4,748,982 | 06/07/88 | Horzewski et al. |
| 4,762,128 | 08/09/88 | Rosenbluth |
| 4,790,315 | 12/13/88 | Mueller, Jr. et al. |
| 4,795,458 | 01/03/89 | Regan |
| 4,830,003 | 05/16/89 | Wolff et al. |
| 4,878,906 | 11/07/89 | Lindemann et al. |
| 4,886,062 | 12/12/89 | Wiktor |
| 4,893,623 | 01/16/90 | Rosenbluth |
| 4,907,336 | 03/13/90 | Gianturco |
| 4,913,141 | 04/03/90 | Hillstead |
| 4,950,227 | 08/21/90 | Savin et al. |
| 4,969,458 | 11/13/90 | Wiktor |
| 4,969,890 | 11/13/90 | Sugita et al. |
| 4,990,155 | 02/05/91 | Wilkoff |
| 4,998,539 | 03/12/91 | Delsanti |
| 5,002,560 | 03/26/91 | Machold et al |

UNITED STATES PATENT AND TRADEMARK OFFICE
CERTIFICATE OF CORRECTION

PATENT NO. : 6,241,758 B1
DATED : June 5, 2001
INVENTOR(S) : Daniel L. Cox

It is certified that error appears in the above-identified patent and that said Letters Patent is hereby corrected as shown below:

| | | |
|---|---|---|
| 5,026,377 | 06/25/91 | Burton et al. |
| 5,034,001 | 07/23/91 | Garrison et al. |
| 5,035,706 | 07/30/91 | Gianturco et al. |
| 5,037,392 | 08/06/91 | Hillstead |
| 5,037,427 | 08/06/91 | Harada et al. |
| 5,041,126 | 08/20/91 | Gianturco |
| 5,059,166 | 10/22/91 | Fischell et al. |
| 5,061,275 | 10/29/91 | Wallsten et al. |
| 5,064,435 | 11/12/91 | Porter |
| 5,071,407 | 12/10/91 | Termin et al. |
| 5,078,720 | 01/07/92 | Burton et al. |
| 5,089,005 | 02/18/92 | Harada |
| 5,089,006 | 02/18/92 | Stiles |
| 5,092,877 | 03/03/92 | Pinchuk |
| 5,108,416 | 04/28/92 | Ryan et al. |
| 5,123,917 | 06/23/92 | Lee |
| 5,135,517 | 08/04/92 | McCoy |
| 5,137,513 | 08/11/92 | McInnes et al. |
| 5,158,548 | 10/27/92 | Lau et al. |
| 5,163,952 | 11/17/92 | Froix |
| 5,163,958 | 11/17/92 | Pinchuk |
| 5,171,262 | 12/15/92 | MacGregor |
| 5,183,085 | 02/02/93 | Timmermans |
| 5,192,297 | 03/09/93 | Hull |
| 5,197,978 | 03/30/93 | Hess |
| 5,222,969 | 06/29/93 | Gillis |
| 5,222,971 | 06/29/93 | Willard et al. |
| 5,226,913 | 07/13/93 | Pinchuk |
| 5,242,451 | 09/07/93 | Harada et al. |
| 5,256,146 | 10/26/93 | Ensminger et al. |
| 5,258,020 | 11/02/93 | Froix |
| 5,263,964 | 11/23/93 | Purdy |
| 5,282,823 | 03/01/94 | Schwartz et al. |
| 5,282,824 | 02/01/94 | Gianturco |
| 5,300,085 | 04/05/94 | Yock |

UNITED STATES PATENT AND TRADEMARK OFFICE
CERTIFICATE OF CORRECTION

PATENT NO.   : 6,241,758 B1
DATED        : June 5, 2001
INVENTOR(S)  : Daniel L. Cox It is certified that error appears in the above-identified patent and that said Letters Patent is hereby corrected as shown below:

| | | |
|---|---|---|
| 5,304,200 | 04/19/94 | Spaulding |
| 5,306,294 | 04/26/94 | Winston et al. |
| 5,354,308 | 10/11/94 | Simon et al. |
| 5,354,309 | 10/11/94 | Schnepp-Pesch et al. |
| 5,372,600 | 12/13/94 | Beyar et al. |
| 5,378,239 | 01/03/95 | Termin et al. |
| 5,395,390 | 03/07/95 | Simon et al. |
| 5,403,341 | 04/04/95 | Solar |
| 5,405,377 | 04/11/95 | Cragg |
| 5,411,507 | 05/02/95 | Heckele |
| 5,415,664 | 05/16/95 | Pinchuk |
| 5,421,955 | 06/06/95 | Lau et al. |
| B1 5,421,955 | 01/20/98 | Lau et al. |
| 5,443,496 | 08/22/95 | Schwartz et al. |
| 5,447,503 | 09/05/95 | Miller |
| 5,449,373 | 09/12/95 | Pinchasik et al. |
| 5,453,090 | 09/26/95 | Martinez et al. |
| 5,456,694 | 10/10/95 | Marin et al. |
| 5,458,615 | 10/17/95 | Klemm et al. |
| 5,478,349 | 12/26/95 | Nicholas |
| 5,484,444 | 01/16/96 | Braunschweiler et al. |

FOREIGN PATENT DOCUMENTS

| | | |
|---|---|---|
| 0 556 940 A1 | 08/25/86 | European Patent Office |
| WO 95/33422 | 12/14/95 | PCT |
| WO 96/39998 | 12/19/96 | PCT |
| WO 98/22159 | 05/28/98 | PCT |

UNITED STATES PATENT AND TRADEMARK OFFICE
CERTIFICATE OF CORRECTION

PATENT NO. : 6,241,758 B1
DATED : June 5, 2001
INVENTOR(S) : Daniel L. Cox

It is certified that error appears in the above-identified patent and that said Letters Patent is hereby corrected as shown below:

OTHER DOCUMENTS

Brochure: Pfizer Schneider Innovation for Life *coronary Wallstent ™Endoprothesis With 5F Rolling Membrane Device (1986)*

Wallace, Michael J., at al., *Tracheobronchial Tree: Experimental Stents Used in Experimental (Work in Progress)*, Radiology, pp. 309-312, Vol. 158, February 1986

Signed and Sealed this

Twenty-seventh Day of November, 2001

*Attest:*

Nicholas P. Godici

*Attesting Officer*

NICHOLAS P. GODICI
*Acting Director of the United States Patent and Trademark Office*